United States Patent [19]

Stroz et al.

[11] Patent Number: 4,457,921
[45] Date of Patent: Jul. 3, 1984

[54] METHOD OF REDUCING DENTAL CARIES

[75] Inventors: John J. Stroz, Monroe, Conn.; Donald A. M. Mackay, Pleasantville, N.Y.

[73] Assignee: Nabisco Brands, Inc., Parsippany, N.J.

[21] Appl. No.: 492,990

[22] Filed: May 9, 1983

Related U.S. Application Data

[63] Continuation of Ser. No. 248,087, Mar. 27, 1981.

[51] Int. Cl.$^3$ ............... A61K 7/16; A61K 31/70
[52] U.S. Cl. .................... 424/180; 424/48; 424/49; 426/3; 426/548; 426/658; 426/661
[58] Field of Search .................... 426/3-6, 426/548, 658, 661; 424/48-58, 180

[56] References Cited

U.S. PATENT DOCUMENTS

| Re. 26,959 | 9/1970 | Conrad et al. | 99/141 |
|---|---|---|---|
| 3,556,811 | 1/1971 | Smith | 99/134 |
| 4,013,775 | 3/1977 | Nelson et al. | 424/361 |
| 4,134,999 | 1/1979 | Muhler et al. | 426/548 |
| 4,208,431 | 6/1980 | Friello et al. | 426/3 |
| 4,217,368 | 8/1980 | Witzel et al. | 426/548 |
| 4,277,464 | 7/1981 | Reussner et al. | 424/54 |
| 4,277,511 | 7/1981 | Bliznak et al. | 426/548 |
| 4,279,931 | 7/1981 | Verwaerde et al. | 426/548 |

FOREIGN PATENT DOCUMENTS 899143   5/1972   Canada .

OTHER PUBLICATIONS

Leroy, "Hydrogenated Starch Hydrolysates," *Health and Sugar Substitutes*, pp. 114–119 (1978).
Zimmerman, "Technological Problems in the Incorporation of Hydrogenated Glucose Syrups and L-Sorbose," *Health and Sugar Substitutes*, pp. 145–152 (1978).
Kearsley and Birch, "Production and Physicochemical Properties of Hydrogenated Glucose Syrups," *Die Starke* 29, pp. 425–429 (1977).

*Primary Examiner*—Shep K. Rose
*Attorney, Agent, or Firm*—Richard Kornutik

[57] ABSTRACT

A method for treating teeth to reduce caries is provided wherein the teeth are contacted with a hydrogenated starch hydrolysate, in the presence of a sugar, for example, as contained in a chewing gum composition or toothpaste or powder composition, the hydrogenated starch hydrolysate and sugar being present in an amount sufficient to inhibit growth of *Streptococcus mutans* in the oral cavity or on the teeth.

8 Claims, No Drawings

METHOD OF REDUCING DENTAL CARIES

This is a continuation of appliation Ser. No. 248,087, filed Mar. 27, 1981.

The present invention relates to a method for preventing or reducing dental caries wherein a hydrogenated starch hydrolysate is employed to inhibit growth of *Streptococcus mutans* in the oral cavity when sucrose is present.

Foods containing natural sugars such as sucrose and glucose have long been recognized as a major contributing cause of dental caries. The sugars are an easily utilizable source of nutrition for plaque forming bacteria, such as *Streptococcus mutans* found in the oral cavity.

Dental decay is initiated by the decalcification of dental enamel by organic acids. These acids are readily produced by fermentative catabolism of dietary carbohydrates by various plaque-forming organisms such as *S. mutans*. Many studies have shown that the consumption of fermentable sugars can result in plaque pH changes below the critical level (pH 5.5) at which enamel starts to dissolve.

In an effort to reduce tooth decay, artificial sweeteners, such as saccharin salts and cyclamate salts have been employed as sugar substitutes in many foods. However, such foods have not been entirely accepted by the consuming public, and especially by children, because of the metallic or bitter after-taste characteristic of the usual forms of artificial sweeteners. The use of non-fermentable carbohydrates, such as polyhydric alcohols like sorbitol, mannitol and xylitol have been employed in place of sugars in chewing gums and confections. Moreover, these non-sugar bulking agents have been found to be physically inferior in taste, stability, and manufacturing ease to the sugar normally used.

It has now been found that the use of hydrogenated starch hydrolysate in combination with natural sugars, in foods, confections, chewing gum, beverages and the like, as well as in toothpaste, powder or polishing compositions, provides an especially effective tool in the fight against dental caries and prevention and inhibition of tooth decay. Surprisingly and unexpectedly, the hydrogenated starch hydrolysate in combination with sucrose has been found to inhibit growth of *Streptococcus mutans* strains of bacteria, such as *Streptococcus mutans* GS-5, a prime contributor to formation of dental plaque and tooth decay. In fact, it has been found that hydrogenated starch hydrolysate inhibits sucrose utilization by *Streptococcus mutans* GS-5.

Thus, in accordance with the present invention, a method is provided for treating teeth to inhibit or prevent caries, wherein the teeth are contacted with a hydrogenated starch hydrolysate in combination with sucrose in amounts sufficient to inhibit growth of *Streptococcus mutans* strains present in the oral cavity or on the teeth.

In a preferred embodiment of the present invention, the hydrogenated starch hydrolysate will be employed together with sucrose or other natural sugar in a weight ratio of hydrogenated starch hydrolysate:sugar of within the range of from about 0.1:1 to about 10:1, and preferably from about 0.25:1 to about 4:1.

The hydrogenated starch hydrolysates employed herein may include those disclosed in Reissue Pat. No. 26,959 or U.S. Pat. No. 3,556,811 as well as various hydrogenated glucose syrups and/or powders which contain sorbitol, hydrogenated disaccharides, hydrogenated tri- to hexa-saccharides, and hydrogenated higher polysaccharides, or mixtures of any two or more of the above.

The hydrogenated glucose syrups and/or powders may be produced by catalytic hydrogenation of standard glucose syrups (acid and/or enzyme converted) to the point where all the glucose end groups of the saccharides are reduced to alcohols, that is, dextrose end groups to sorbitol end groups. In the case of hydrogenated glucose syrups, the total solids are made of from about 4 to about 30% sorbitol, from about 5 to about 65% hydrogenated disaccharides (that is, maltitol), from about 15 to about 75% tri- to hepta-hydrogenated saccharides, and from about 10 to about 65% hydrogenated saccharides higher than hepta.

Examples of particularly suitable hydrogenated starch hydrolysates include from about 6 to about 10% sorbitol, from about 25 to about 55% hydrogenated disaccharides, from about 20 to about 40% hydrogenated tri- to hepta-saccharides, and from about 15 to about 30% hydrogenated saccharides higher than hepta.

Another example of suitable hydrogenated starch hydrolysates includes from about 8 to about 20% sorbitol, from about 5 to about 15% hydrogenated disaccharides, and from about 2 to about 75% hydrogenated tri- to penta-saccharides.

Particularly preferred are hydrogenated starch hydrolysates of the following compositions.

| | Parts by Weight | | |
|---|---|---|---|
| | 1 | 2 | 3 |
| Sorbitol | 10.5 | 17 | 15 |
| Hydrogenated disaccharides | 7.5 | 13 | 10 |
| Hydrogenated tri- to penta-saccharides | 20 | 70 | 40 |
| Hydrogenated saccharides higher than penta and higher saccharide alcohols | 62 | | 35 |

| | 4 | 5 | 6 | 7 |
|---|---|---|---|---|
| Sorbitol | 5–8 | 6–8 | 6–8 | 5–8 |
| Hydrogenated disaccharides | 50–58 | 40–45 | 24–30 | 25–58 |
| Hydrogenated tri- to hexa-saccharides | 20–25 | 25–30 | 35–40 | 20–40 |
| Hydrogenated saccharides higher than hexa | 15–20 | 20–25 | 25–30 | 15–30 |

In carrying out the method of the invention, the hydrogenated starch hydrolysate-sucrose combination will usually be employed in conjunction with a nontoxic edible carrier to form a food, confection, chewing gum, dental tablet, cream or paste, beverage and the like. Regardless of the form of the composition or carrier, the total amount of hydrogenated starch hydrolysate present in the composition will preferably be beyond the normal organoleptic threshold of sweetness. Thus, the hydrogenated starch hydrolysate may be employed in amounts ranging from about 10 to about 90% or more by weight, and preferably from about 12 to about 80% by weight of the total composition while the sucrose will be employed in amounts ranging from about 90 to about 10%, and preferably from about 80 to about 12% by weight of the composition.

It appears that the effectiveness of the hydrogenated starch hydrolysate in inhibiting plaque formation increased with increasing teeth exposure or contact time.

Thus, the presence of relatively small amounts of hydrogenated starch hydrolysate (with sucrose) solubilized in the saliva over extended periods of time (for example 1 to 900 mg hydrogenated starch hydrolysate with sucrose) over a period of 5, 10, 20, 30 minutes or more) is, for the purposes of the present invention, more desirable than the presence of large or peak amounts of hydrogenated starch hydrolysate (and sucrose) solubilized in the saliva for relatively short periods of time (for example, 1 to 900 mg hydrogenated starch hydrolysate over a period of 1 to 4 minutes). Thus, the hydrogenated starch hydrolysate (and sucrose) will preferably be provided in a form or composition so that it may be controlledly or slowly released and solubilized in relatively small quantities in the saliva over extended periods of time; moreover, although large amounts of hydrogenated starch hydrolysate may be initially present, at any given time, amounts of hydrogenated starch hydrolysate which are organoleptically acceptable (that is, below the undesirably oversweet threshold) will be solubilized in the saliva and available for tasting.

Regardless of the form of the hydrogenated starch hydrolysate-sucrose-containing composition, whether it be a chewing gum or otherwise, herein, since the sugar, by itself, contributes to formation of dental plaque, the hydrogenated starch hydrolysate may be said to function as an anti-plaque antidote to sugar and inhibit plaque formation. It has been found that the hydrogenated starch hydrolysates are non-cariogenic because they are only slightly (or not at all) fermented by cariogenic oral microorganisms and inhibit sucrose utilization by *Streptococcus mutans* (especially strain CS-5).

The term "natural sugar" includes sugar alcohols, such as xylitol, sorbitol or mannitol as well as one or more sugars or sugar containing materials, for example, monosaccharides, disaccharides and polysaccharides, some examples of which follow:

monosaccharides of 5 or 6 carbon atoms, such as arabinose, xylose, ribose, glucose, mannose, galactose, fructose, dextrose, or sorbose or mixtures of two or more of the foregoing monosaccharides;

disaccharides, such as sucrose such as cane or beet sugar, lactose, maltose or cellobiose; and polysaccharides, such as partially hydrolyzed starch, dextrin or corn syrup solids.

As indicated, the hydrogenated starch hydrolysate-sugar combination may be incorporated into a chewing gum. Such chewing gum includes gum base, and as a plasticizer-sweetener combination, a hydrogenated starch hydrolysate, for example, as disclosed in Reissue Pat. No. 26,959 and U.S. Pat. No. 3,566,811, or xylitol, sucrose, and optionally sorbitol, and/or a natural sugar, optionally one or more other sugar alcohols, such as mannitol; optionally one or more additional sweetening agents, such as sugar and/or non-sugar sweeteners; and optionally additional flavoring materials, one or more softeners, emulsifiers and/or filters.

The preferred chewing gum composition suitable for use in the method of the present invention comprises a chewing gum wherein the hydrogenated starch hydrolysate is employed in combination with a natural sugar, such as sucrose.

The chewing gum containing hydrogenated starch hydrolysate and sugar employed in the method of the invention may be prepared by mixing melted gum base (heated at, for example, 160°-170° F.) and color, adding about one-third of the hydrogenated starch hydrolysate and mixing for 1 to 3 minutes, if desired, adding polyol, such as mannitol, to the mix, and mixing for 1-5 minutes, adding sucrose, and softener, such as lecithin, flavor, and glycerin (where employed), and when a smooth mixture is obtained, optionally, adding sorbitol solution or corn syrup, then adding the remaining hydrogenated starch hydrolysate alone or with gum arabic, and then optionally adding spray-dried flavor and mixing the entire mass for 2 to 5 minutes.

If desired, the above may be mixed with one or more easily extractable water-soluble sweeteners, such as soluble saccharin salts, aspartame, water-soluble food acid and/or flavors. The resulting mix is then formed into sticks or tablets of chewing gum employing conventional techniques.

Examples of chewing gum formulations which may be employed in the method of the present invention are as follows:

|  | Parts by Weight |
| --- | --- |
| Gum base | 17-30 |
| Sucrose | 50-85 |
| Hydrogenated starch hydrolysate (dry basis) | 12-20 |
| Softener (lecithin) | 0-1.5 |
| Flavor | 0.3-2 |

Other examples of preferred chewing gums for use in the method of the invention are set out in U.S. Pat. No. 4,208,431 the disclosure of which is incorporated herein by reference.

The following in vitro tests were carried out to show that hydrogenated starch hydrolysate inhibits growth of *Streptococcus mutans:*

BRIEF DESCRIPTION OF TEST

In order to investigate the possibility that extracellular polysaccharide (EPS) production from sucrose may be altered by the presence of a second carbohydrate, *Streptococcus mutans* strain GS5 is grown in a chemically defined medium (FMC, Terleckyj et al, Inf. and Immun., 11: 649-655, 1975) supplemented with combinations of sucrose with hydrogenated starch hydrolysate (78% solids, including 6% sorbitol and 50% maltitol). Growth is monitored by turbidity and final growth estimated as total bacterial protein. Terminal pH is also recorded. After 72 hours incubation, EPS is precipitated with ethanol, washed, hydrolysed and assayed as glucose. Under these conditions, in FMC medium, no water-insoluble EPS is obtained. Thus, only water-soluble EPS is assayed. Glucosyltransferase (GTase) and fructosyltransferase (FTase) activities from glucose grown cultures are assayed for their ability to polymerize radiolabelled EPS from radiolabelled sucrose in the presence of the hydrogenated starch hydrolysate.

MATERIALS AND METHODS

Organisms and Growth Conditions

*S. mutans* GS-5 is maintained by weekly or biweekly transfer on Trypticase Soy Agar Plates. It is incubated anaerobically overnight and stored at 4° C. Bacteria are grown in the FMC medium mentioned above. Growth is monitored by absorbance measurements at 700 nm or by protein content.

Protein Assay, Modified Biuret

The pellet precipitate is transferred to a calibrated glass tube. 1M KOH is added to the precipitate to a final volume of 4.5 ml. The test tubes are covered with protein free glass marbles, placed in a 100° C. water bath for 5 minutes and, then, 1 ml of 2.5% $CuSO_4.5H_2O$ is added and the mixture is thoroughly agitated. After standing for 5 minutes, at room temperature, the solutions are centrifuged for 5 minutes at 3,000 rpm. Absorbance of the clear supernatant is read at 555 nm in the spectrophotometer and compared with known standard samples.

Glucose Assay

The pellet precipitate is placed in a calibrated glass tube and resuspended with 2M $H_2SO_4$ to a final volume of 4.5 ml. The tubes are covered with glass marbles and placed in a 100° C. water bath for 120 minutes. After cooling, 100 μl of each hydrolysed solution is pipetted into test tubes and 5.0 ml of o-toluidine is added. This mixture is placed into a boiling water bath for 10 minutes and cooled. The absorbance is read in a spectrophotometer (Beckman/DU) at 635 nm within 30 minutes. Standards are run with the experimental samples.

Fractionation of EPS

Through a series of centrifugations, the EPS is fractionated as follows:

i. The culture is centrifuged to yield a precipitate (bacterial cells and water-insoluble EPS) and supernatant (CDM, "sugars" and water-soluble EPS).

ii. 175 ml of 100% absolute ethanol is added to the decanted supernatant, and this mixture is refrigerated overnight. The mixture is then centrifuged, the supernatant poured off and the pellet is retrieved for the glucose assay (detail follows). This precipitate represents water-soluble EPS.

The cell pellet of centrifugation I is agitated and resuspended in 70 ml of 1M KOH. This procedure allows the water-insoluble EPS to be redissolved in alkali.

iii. This solution is centrifuged and the supernatant is poured off, and 175 ml of 100% absolute ethanol is added and refrigerated overnight. The precipitate of centrifugation III represents the washed whole cells from the original culture. This precipitate is assayed as protein by the modified biuret method.

iv. The refrigerated solution is centrifuged, but under these growth conditions of this experiment, no water-insoluble EPS is found.

Initial Growth and EPS Studies

The effect of sucrose concentration in the growth medium is determined. The final optical density of cultures of S. mutans GS-5 indicated that near optimal growth occurred with 0.4 to 0.5% sucrose. Additional sucrose, up to 2% resulted in only slight increase in growth. Concurrently, the major pH drop also was seen with 0.4 to 0.5% sucrose.

It was therefore necessary to use sucrose concentrations of 0.4% or more in experiments with combined carbohydrates so that any decrease in growth could be attributed to inhibition by the test sweetener and not merely by the replacement of sucrose by non-metabolized carbohydrate.

In the initial studies, growth in the presence of excess sucrose was inhibited by hydrogenated starch hydrolysate.

Cell growth, total cellular protein and EPS were determined for 20/80 mixtures of sucrose/hydrogenated starch hydrolysate. See Table I. Again, hydrogenated starch hydrolysate inhibited growth of S. mutans GS-5. Both optical density and protein determinations confirmed this. No extracellular polysaccharide production was detected in the hydrogenated starch hydrolysate supplemented cultures. This was expected since no cell growth occurred. Supplementation with glucose resulted in a doubling of EPS synthesis.

Detailed growth studies were undertaken with hydrogenated starch hydrolysate as a sugar supplement. In these experiments, sucrose/sugar substitute ratios of 20/80, or 50/50 or 80/20 were used at final carbohydrate concentrations up to 2%. A complicating factor throughout these studies was the difference in observed growth due to total carbohydrate concentration. In order to maintain a final carbohydrate at any given level, a non-metabolizable, non-inhibitory carbohydrate was needed. In the studies with S. mutans GS-5, arabinose was used to replace hydrogenated starch hydrolysate.

S. mutans GS-5 was dramatically inhibited by hydrogenated starch hydrolysate in the growth medium. Arabinose was added to sucrose control cultures to maintain the 2% final carbohydrate concentration. Arabinose did not affect growth of S. mutans GS-5 in 0/100, 50/50 or 20/80 mixtures with sucrose. In 20/80 or 50/50 combination, hydrogenated starch hydrolysate dramatically inhibited growth. At 80/20 combination, hydrogenated starch hydrolysate essentially blocked cell division. From these experiments it can be seen that the hydrogenated starch hydrolysate has substantial, strain specific, antimicrobial activity.

TABLE I

| Sweetener | Growth | Protein Assay | Glucose Assay |
|---|---|---|---|
| Final Concentration 2.0% Ratio - 20:80 Sucrose:Hydrogenated Starch hydrolysate | S. Mutans 70 hours in C.D.M. | Mg protein per 70 ml culture average | $H_2O$ Soluble EPS absorbance average |
| Sucrose | + | 493 | 429~100 |
| Sucrose/hydrogenated starch hydrolysate | + | 0 | 0 |
| Chemically defined medium | − | 0 | 0 |

The following Examples illustrate preferred embodiments of the present invention without, however, limiting the same thereto. All temperatures are expressed in °F.

EXAMPLE 1

A cherry flavor hydrogenated starch hydrolysate-sugar-containing chewing gum is prepared from the following ingredients;

| Ingredients | Parts by Weight |
|---|---|
| Gum base | 20 |
| Sugar | 50 |
| Hydrogenated starch hydrolysate powder (78% solids, including 6% sorbitol and 56% maltitol) | 16 |
| Dextrose | 10 |
| Lecithin | 0.2 |

| Ingredients | Parts by Weight |
| --- | --- |
| Citric acid | 0.5 |
| Fumaric acid (passes through a U.S. 140 mesh screen) | 2 |
| Free saccharin acid (passes through a U.S. 140 mesh screen) | 0.2 |
| Artificial cherry flavor | 1 |
| Gum arabic coated cherry flavor | 1.5 |

The gum base is melted (temperature 270°) and placed in a standard dough mixer kettle equipped with sigma blades. The hydrogenated starch hydrolysate and lecithin are added and mixed for 2 minutes at 200°. At the time the mix is folding well, powdered free saccharin and powdered fumaric acid are added to the base-syrup mix and the mixture is mixed for 1 minute at 200°. Thereafter, the sucrose, dextrose, flavor oil, citric acid, and coloring agents are added and blended with the above mixture for 5 minutes at 160°. The resulting gum is discharged from the kettle and formed into gum sticks employing conventional techniques.

The chewing gum product obtained is found to have a pleasant balanced sweet-sour taste for up to 30 minutes and is effective in inhibiting growth of *Streptococcus mutans* in the oral cavity.

EXAMPLE 2

A peppermint flavor hydrogenated starch hydrolysate-sugar-containing chewing gum is prepared from the following ingredients:

| Ingredients | Parts by Weight |
| --- | --- |
| Gum base | 20 |
| Hydrogenated starch hydrolysate (as described in Ex. 1) | 17 |
| Powdered Sugar (sucrose) | 50 |
| Dextrose | 10 |
| Peppermint oil | 1 |
| Lecithin | 0.2 |

The gum base is melted (temperature 270°) and placed in a standard dough mixer kettle equipped with sigma blades. The hydrogenated starch hydrolysate and lecithin are added and mixed for 2 minutes at 200°. At the time the mix is folding well, the sucrose, dextrose and flavor oil are added during which time the mixture is mixed another 3 minutes at 200°. Thereafter, the sucrose, dextrose and flavor oil are added during which time the mixture is mixed for 5 minutes. The gum is then discharged from the kettle, cut into 25 lb. loaves and allowed to cool to 90°–120° F. It is then rolled to a thickness of 0.178 cm on a standard Gimpel machine and scored into strips 7.26 cm wide and 41.9 cm long, and cooled for 12–18 hours.

The chewing gum product obtained is found to have a pleasant sweet taste for up to 30 minutes and inhibits growth of *Streptococcus mutans* in the oral cavity.

EXAMPLE 3

A spearmint flavor hydrogenated starch hydrolysate-sugar-containing chewing gum is prepared from the following ingredients:

| Ingredient | Parts by Weight |
| --- | --- |
| Gum base | 20 |
| Sugar (sucrose) | 52 |
| Corn syrup 44 Be' | 4 |
| Dextrose | 10 |
| Lecithin | 0.2 |
| Hydrogenated starch hydrolysate (as described in Ex. 1) | 12 |
| Spearmint oil | 0.6 |

The gum base is melted (temperature 270° F.) and placed in a standard dough mixer kettle equipped with sigma blades. The corn syrup and lecithin are added and mixed for 2 minutes at 200°. At the time the mix is folding well, hydrogenated starch hydrolysate and flavor oil are mixed for 1 minute at 200°. Thereafter, the sucrose, dextrose and coloring agents are added and blended with the above mixture for 5 minutes at 160°. The resulting gum is discharged from the kettle and formed into gum sticks as described in EXAMPLE 1.

The chewing gum product obtained is found to have a pleasant sweet taste for up to 30 minutes and inhibits growth of *Streptococcus mutans* in the oral cavity.

What is claimed is:

1. In a method of essentially blocking cell division and thereby inhibiting the growth of *Streptococcus mutans* having near optimum growth occurring in an environment of 0.4 to 0.5% of sucrose, with a slight increase in said growth resulting with an increase of the sucrose concentration to up to 2.0%, the improvement comprising, at a sucrose concentration of 0.4% or more, reducing the level of extracellular polysaccharide production from said sucrose by said *Streptococcus mutans* with a synergistic amount, in the range of from about 0.25:1.0 to about 4.0:1.0 of a sucrose to sugar substitute ratio at a final carbohydrate concentration of up to 2.0%, of hydrogenated starch hydrolysate non-metabolizing carbohydrate sugar substitute which thereby inhibits or prevents the growth of EPS production from said sucrose by said *Streptococcus mutans* to an extent greater than that achieved merely by replacement of said sucrose by non-metabolized carbohydrate.

2. The improvement of claim 1 wherein said ratio of hydrogenated starch hydrolysate to sucrose is 4.0:1.0.

3. The improvement of claim 1 wherein said hydrogenated starch hydrolysate is prepared by hydrogenating saccharified starch having a dextrose equivalent of 15–75% and containing dextrines until substantially no dextrose and maltose remain.

4. The improvement of claim 1 wherein said hydrogenated starch hydrolysate comprises from about 72% to about 80% of solids of which from about 4 to about 20% is sorbitol, from about 5 to about 65% is hydrogenated disaccharides, from about 15 to about 75% is tri- to hepta-hydrogenated saccharides, and from about 10 to about 65% is hydrogenated saccharides higher than hepta.

5. The improvement of claim 1 wherein said solids portion of said hydrogenated starch hydrolysate contains from about 6 to about 10% sorbitol, and from about 25 to about 55% by weight hydrogenated disaccharides, from about 20 to about 40% hydrogenated tri- to hepta-saccharides, and from about 15 to about 30% hydrogenated saccharides higher than hepta.

6. The improvement of claim 1 wherein said solids portion of said hydrogenated starch hydrolysate contains from about 8 to about 20% sorbitol, and from about 5 to about 15% by weight hydrogenated disaccharides, and from about 20 to about 75% hydrogenated tri- to penta-saccharides.

7. The improvement of claim 1 wherein said hydrogenated starch hydrolysate comprises from about 5 to about 8% sorbitol, from about 25 to about 58% hydrogenated disaccharides, from about 20 to about 40% hydrogenated tri- to hexa-saccharides and from about 15 to about 30% hydrogenated saccharides higher than hexa.

8. The improvement of claim 1 wherein said *Streptococcus mutans* is contacted with the sucrose/hydrogenated starch hydrolysate combination for a time of from about 5 to about 30 minutes.

* * * * *